United States Patent [19]

Berthod et al.

[11] 4,446,051

[45] May 1, 1984

[54] WATER-IN-OIL EMULSIONS

[75] Inventors: Daniel P. M. Berthod, Paris; Simone Ferret, St. Denis, both of France

[73] Assignee: Lever Brothers Company, New York, N.Y.

[21] Appl. No.: 298,563

[22] Filed: Sep. 2, 1981

[30] Foreign Application Priority Data

Sep. 15, 1980 [EP] European Pat. Off. ........... 80303230

[51] Int. Cl.³ .................... B01J 13/00; A01N 61/02; A61K 31/00; A61K 47/00
[52] U.S. Cl. .................................. 252/309; 424/169; 424/172
[58] Field of Search ................ 252/309; 424/169, 172

[56] References Cited

U.S. PATENT DOCUMENTS 2,948,686  8/1960  Gianladis ........................... 252/309
4,350,605  9/1982  Hughett ............................. 252/305
4,372,944  2/1983  Herrold ............................. 424/83

FOREIGN PATENT DOCUMENTS 9404     4/1980  European Pat. Off. .
2409081  6/1979  France .
2419758  10/1979 France .
883254   11/1961 United Kingdom .
2009617  6/1979  United Kingdom .
2021411  12/1979 United Kingdom .

OTHER PUBLICATIONS

Berthod, Benzoni, & Gautier, "Water-in-Oil Emulsions and Process . . . ,".
Janistyn, "Handbook of Cosmetics and Perfumes," 3rd Edition, vol. 1, 1978, pp. 617–618.

Primary Examiner—Richard D. Lovering
Assistant Examiner—Catherine S. Kilby
Attorney, Agent, or Firm—Amirali Y. Haidri; James J. Farrell

[57] ABSTRACT

A high internal phase water-in-oil emulsion comprises, in addition to water, a branched chain non-polar oil, a non-anionic liquid emulsifier having an HLB value of from 1 to 7, and a special montmorillonite clay derivative and a water-soluble salt of magnesium which together stabilize the emulsion. The emulsion is particularly suitable as a cosmetic cream for topical application to the skin.

16 Claims, No Drawings

WATER-IN-OIL EMULSIONS

The invention relates to emulsions. More particularly, the invention relates to high internal phase water-in-oil emulsions suitable for the preparation of cosmetic, pharmaceutical and other products and to methods for the preparation of such emulsions.

By "high internal phase emulsion" is meant an emulsion in which the volume of the internal phase occupies at least 75% of the total volume of the emulsion.

Water-in-oil emulsions, other than high internal phase emulsions, have been employed in the formulation of cosmetic and pharmaceutical ointments, emollient creams, lotions and the like. However, while such emulsions can impart desirable characteristics of water-repellancy to the skin and provide a means whereby fats, oils and waxes can be absorbed onto human skin, the use of such emulsions in skin treatment products has sometimes been precluded because they have been implicated in toxicity, skin irritancy or excessive greasiness in use. The problem of instability has also limited the use of high internal phase water-in-oil emulsions in cosmetics and pharmaceutical products where storage stability is a pre-requisite.

A study was accordingly undertaken to examine the instability of these emulsions and to establish means whereby stability could be improved. It was found, for example, that high internal phase water-in-oil emulsions containing as skin benefit agents a water-soluble metallic salt dissolved in the aqueous phase, are stable for no more than a few days. Syneresis of the internal phase or even separation of the oily and aqueous phases can then generally be seen as an accumulation of oil at the surface of the emulsion.

This problem has led to the screening of many substances in a search for a stabilising agent whose incorporation in a product based on a high internal phase emulsion would effectively extend the shelf-life of that product at normal storage temperatures.

It has now been discovered that this problem of instability of the high internal phase emulsion on storage can be overcome by incorporating into the emulsion, in addition to a water-soluble metallic salt, a special montmorillonite clay derivative. The high internal phase emulsions so obtained have excellent storage characteristics in that the water and oil phases do not separate when the emulsion is stored for at least three months, even at a "tropical" temperature of 50° C., or when subjected repeatedly to freezing at a temperature of −10° and thawing at ambient temperature of +20° C.

These high internal phase emulsions are accordingly suitable for use in the preparation of cosmetic and pharmaceutical products and the like, particularly for topical application to human skin. They lack the aforementioned disadvantages in that they are non-toxic, non-irritating to the skin, not excessively greasy in use and do not suffer from instability on storage.

It has also been observed that inclusion of the special montmorillonite clay derivative in the emulsion unexpectedly provides a further benefit in addition to that of imparting a very high degree of stability to the emulsion after manufacture and during storage, and that is enabling the emulsion to "break" almost instantly when applied topically to human skin, thus permitting any skin benefit ingredient in the emulsion to be more readily available for uptake by the skin.

The stability imparted by the special montmorillonite clay derivative is all the more surprising when it is realised how intrinsically unstable are high internal phase water-in-oil emulsions. It is accordingly totally unexpected that the special montmorillonite clay derivative should exhibit, as we have shown, on the one hand stability of the emulsion in its container, while on the other hand allowing the emulsion to "break" when applied topically to the skin.

Accordingly, the invention provides a high internal phase water-in-oil emulsion, characterised in that it comprises in addition to water:
(a) a branched chain non-polar oil;
(b) a non-anionic liquid emulsifier having an HLB value of from 1 to 7;
(c) a reaction product of sodium magnesium-fluorolithosilicate trioctahedral montmorillonite clay and the quaternary ammonium salt having the formula:

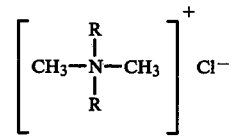

where R represents hydrogenated tallow fatty acid radicals; and
(d) a water soluble salt of magnesium.

The invention also provides a process for preparing a high internal phase water-in-oil emulsion which comprises the steps of:
(a) mixing the reaction product of a sodium magnesium-fluorolithosilicate trioctahedral montmorillonite clay and the quaternary ammonium salt having the formula:

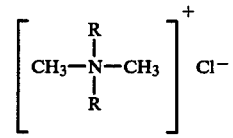

where R represents hydrogenated tallow fatty acid radicals, with a non-anionic liquid emulsifier having an HLB value of from 1 to 7 and a branched chain non-polar oil to provide an oily phase; and
(b) homogenising the oily phase with an aqueous phase comprising an aqueous solution of a salt of magnesium and other water soluble ingredients to provide a water-in-oil emulsion in which the aqueous phase forms from 75 to 98% by volume of the emulsion and the oily phase forms from 2 to 25% by volume of the emulsion.

The emulsion according to the invention consists of an internal phase which is aqueous and an external phase which is oily. It should be explained that water-in-oil emulsions which are not high internal phase emulsions usually consist of from about 1 to 74% by volume of an aqueous phase dispersed in about 99 to 26% by volume of an oily phase. A water-in-oil emulsion consisting of 74% by volume aqueous phase and 26% by volume oily phase represents the theoretical maximum packing volume concentration of rigid monodisperse spheres of water as the internal phase in oil as the external phase. Hence, water-in-oil emulsions containing more than 74% aqueous phase are high internal phase emulsions.

The water-in-oil emulsion of the invention comprises from 75 to 98%, preferably 80 to 97% by volume of an aqueous phase and from 2 to 25%, preferably 3 to 20% by volume of an oily phase respectively.

In order to obtain optimum stability of the high internal phase water-in-oil emulsions, it has been shown necessary to select carefully the oil ingredient, the emulsifier and to employ a special montmorillonite clay derivative as a special emulsion stabiliser with the magnesium salt to ensure that the emulsions once made generally remain stable over an extended period of time.

The Oil

The oil should preferably be liquid at room temperature (20° C.) and should be cosmetically and pharmaceutically acceptable. It is however also possible to employ waxes which can be solid at room temperature. The oil, other oily material and wax are herein referred to as "oil".

The oil should also be non-polar and should contain branched chain alkyl groups. The preferred oils are highly branched-chain mineral oils.

Examples of preferred oils are (in decreasing order of preference):

$C_{10}$ to $C_{12}$ isoparaffins such as ISOPAR L (Esso)
Polyisobutene such as PARLEAM (Nichiyu)
Squalene such as COSBIOL (Laserson & Sabetay)
Branched chain light paraffin oil such as LYTOL (Witko) or WMl (BP)
Mineral oil such as MARCOL 82 (Esso) or CARNATION OIL (Witko)
Petrolactum such as VASELINE (Gerland)
Microcrystalline wax such as CEREWAX L (La Ceresine)
Lanolin derivatives such as MODULAN (Amerchol)
Oleic decylester such as CETIOL V (Henkel)
Ethyl hexylpalmitate such as WICKENOL 155
$C_{16}$ to $C_{18}$ fatty alcohol di-isooctanoate such as CETIOL SN (Henkel)

It is also possible to employ vegetable and animal oils, provided that branched-chain alkyl groups are present.

The quantity of oil in the emulsion is from 1.4 to 24.3%, preferably from 2 to 24%, and most preferably from 2 to 15% by weight of the emulsion.

If the emulsion contains less than 1.4% oil, it is generally not possible to obtain a stable water-in-oil emulsion, whereas if the emulsion contains more than 24.3% oil, then the emulsion will cease to exhibit the special properties and characteristics attributable to a high internal phase emulsion.

The Emulsifier

The emulsifier should be liquid at room temperature (20° C.) and be cosmetically and pharmaceutically acceptable; it should also not be anionic in character, otherwise there is a possibility that it will interfere with the stabilising effect of the montmorillonite clay which is cationic in character.

The emulsifier should have an HLB value of from 1 to 7, preferably from 2 to 6.

Examples of suitable emulsifiers are (in decreasing order of preference):

| | HLB Value |
|---|---|
| ARLACEL 987 (sorbitan isostearate) by Atlas | 4.3 |
| MONTANE 70 (sorbitan isostearate) by Seppic | 4.3 |
| CRILL 6 (sorbitan isostearate) by Croda | 4.3 |

-continued

| | HLB Value |
|---|---|
| IMWITOR 780K (glycerol monoisostearate) by Witko | 3.7 |
| BRIJ 92 (polyoxyethylene(2)oleyl ether) by Atlas | 4.9 |
| Triglycerol monooleate by PVO International | 4.0 |
| ARLACEL 80 (sorbitan monooleate) by Atlas | 4.3 |
| ARLACEL 83 (sorbitan sesquioleate) by Atlas | 3.7 |
| ARLACEL 85 (sorbitan trioleate) by Atlas | 1.8 |
| Decaglycerol tetraoleate by PVO International | 6.0 |
| Decaglycerol octaoleate by PVO International | 4.0 |
| SIMULSOL 92 (polyethoxylated(2)oleyl alcohol) by Produits Chimiques de la Montagne Noire | 6.7 |

The quantity of emulsifier in the emulsion is from 0.5 to 10%, preferably 2 to 5% by weight of the emulsion.

If the emulsion contains less than 0.5% of emulsifier, it is unlikely that the emulsion, if obtained, will remain stable on storage, whereas if the emulsion contains more than 10% of emulsifier, the stability of the emulsion can be adversely affected.

The special montmorillonite clay derivative

The special montmorillonite clay derivative is a reaction product of a sodium magnesium-fluorolithosilicate trioctahedral montmorillonite clay and the quaternary ammonium salt having the formula:

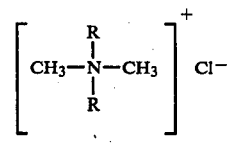

where R represents hydrogenated tallow fatty acid radicals.

This montmorillonite clay derivative is hereinafter referred to as Quaternium-18 Hectorite. An example of Quaternium-18 Hectorite is BENTONE 38 available from National Lead Industries.

The quantity of Quaternium-18 Hectorite in the emulsion is from 0.1 to 5%, preferably 0.1 to 1% by weight of the emulsion.

If the emulsion contains less than 0.1% of the Quaternium-18 Hectorite, it is unlikely that the emulsion will remain stable on storage, whereas if the emulsion contains more than 5% Quaternium-18 Hectorite, the emulsion is likely to be too viscous to employ as a cosmetic or pharmaceutical product, particularly for topical application to the skin.

The water soluble magnesium salt

The emulsion of the invention also comprises a water-soluble magnesium salt which not only serves to provide an additional cosmetic benefit to the emulsion when applied topically to human skin, but which also further enhances the stability of the emulsion during storage after manufacture and before use.

Thus, it has been shown that water-in-oil high internal phase emulsions comprising a branched chain non-polar oil, a non-anionic liquid emulsifier and the montmorillonite clay, but without magnesium salt in the aqueous phase, are stable under ambient storage conditions for only a few days or weeks. The further incorporation of a water-soluble magnesium salt into such a high internal phase emulsion dramatically enhances their stability such that they can remain stable, even at a storage temperature of from −5° C. to 60° C., for many months or even years without showing any sign of syneresis.

Accordingly, it is an important feature of the invention that the water-in-oil high internal phase emulsions comprise both the montmorillonite clay, as herein described, and the water-soluble salt of magnesium.

The water soluble salt of magnesium

Examples of suitable water-soluble salts of magnesium are magnesium sulphate, magnesium sulphate heptahydrate, magnesium sulphate monohydrate, magnesium acetate, magnesium bromide, magnesium bromide hexahydrate, magnesium chloride, magnesium chloride hexahydrate, magnesium iodide, magnesium iodide octahydrate and magnesium nitrate hexahydrate. The preferred magnesium salt is magnesium sulphate heptahydrate.

The quantity of the water-soluble magnesium salt present in the emulsion will usually be from 0.1 to 5%, preferably from 0.1 to 2% by weight of the emulsion; the actual amount employed will depend on which magnesium salt is selected. As a general rule it can be stated that the concentration of the water-soluble magnesium salt in terms of the emulsion will be from 0.003 to 0.5 M.

If the emulsion contains less than 0.1% by weight of the magnesium salt, it is unlikely that the stability of the emulsion will be improved beyond that due to the presence of the Quaternium-18 Hectorite, whereas if the emulsion contains more than 5% by weight of the magnesium salt, it is unlikely that the stabilisation of the emulsion can be further enhanced.

Water

The emulsion also comprises water. The quantity of water in the emulsion is from 0.1 to 97.9%, preferably 1 to 97, most preferably 60 to 95% by weight of the emulsion.

If the emulsion contains more than 97.9% of water, the stability of the emulsion on storage is likely to be poor and syneresis can occur.

Cosmetically and Pharmaceutically Active Ingredients

The emulsion according to the invention can be employed as a vehicle for a wide variety of cosmetically or pharmaceutically active ingredients, particularly ingredients which have some beneficial effect when applied to the skin.

The emulsion thus provides a means whereby such active ingredients can be diluted, preserved, conveyed to and distributed on the skin surface at an appropriate concentration.

Especially preferred examples of active ingredients include moisturisers such as: sodium pyrollidone carboxylate, sodium lactate, lactic acid, triethanolamine lactate and sodium chloride.

Examples of other active ingredients that can also be employed include sunscreen agents, germicides, deodorants, antiperspirants, healing agents.

Functional Adjuncts

The emulsion according to the invention can also contain functional adjuncts for further controlling the properties of a pharmaceutical or cosmetic composition containing the emulsion. Functional adjuncts include: antioxidants, propellants, solvents, humectants, thickeners and emolients.

Preparation of emulsion

The high internal phase water-in-oil emulsions of the invention can be prepared by mixing the Quaternium-18 Hectorite with the liquid emulsifier having an HLB value of from 1 to 7 and the oil to provide an oily phase and subsequently homogenising from 2 to 25 parts by volume of the oily phase with from 75 to 98 parts by volume of the aqueous phase containing the water-soluble magnesium salt and other water soluble ingredients, if any, to provide the emulsion.

Product Forms

The compositions of the invention can be liquid, for example products such as lotions for use in conjunction with applicators such as a roll-ball applicator or a spray device such as an aerosol can containing propellants or a container fitted with a pump to dispense the product. Alternatively, the compositions of the invention can be solid or semi-solid, for example powders, moulded sticks, creams or gels, for use in conjunction with an applicator such as a powder sifter or a stick applicator, or simply a tube or lidded jars.

The invention accordingly also provides a closed container containing a cosmetically acceptable composition as herein defined.

The invention is illustrated by the following examples:

EXAMPLE 1

This example illustrates a high internal phase water-in-oil emulsion moisturising cream (w/o HIPE cream) for topical application to the skin.

This w/o HIPE cream contained the following ingredients:

| | | % w/w |
|---|---|---|
| (a) | branched chain non-polar oils: | |
| | (i) CARNATION OIL (a light liquid paraffin available from Witco) | 5.0 |
| | (ii) Oleic acid decylester (CETIOL V available from Henkel) | 5.0 |
| (b) | a liquid emulsifier having an HLB value of from 1 to 7: | |
| | Sorbitan isostearate (ARLACEL 987 available from Atlas) | 2.5 |
| (c) | Quaternium-18 Hectorite: | |
| | BENTONE 38 (available from National Lead Industries) | 0.5 |
| (d) | Magnesium salt: | |
| | Magnesium sulphate heptahydrate | 0.3 |
| (e) | Emollient, moisturising, electrolyte preservative and perfume | 9.5 |
| (f) | Water: | |
| | Deionised water | 77.2 |

The oils were mixed with the emulsifier, the Quaternium-18 Hectorite and the preservative to provide the oily phase. The aqueous phase containing water, the magnesium sulphate heptahydrate and the emollient and moisturising electrolyte was then added slowly at first and then more rapidly to the oily phase with stirring until an emulsion in the form of a white cream was obtained. The mixing step was carried out at room temperature, i.e. at about 23° C. Finally the perfume was distributed throughout the emulsion.

In order to test the stability of the cream, samples were stored at 23° C., 35° C., 42° C. and at 50° C. After more than six months' storage, there was no sign in any of the samples of syneresis or breakdown of the emulsion. Likewise, repeated freeze-thaw cycling from −5° C. to +42° C. did not indicate any such instability in the product.

The product was accordingly judged completely stable and suitable for sale to consumers.

When applied to the human skin, the product has a pleasant creamy texture, is easily distributed topically and "breaks" on contact with the skin. The release of the aqueous phase gives the consumer a pleasant fresh sensation which is judged as signalling a moisturising effect.

The superiority of this product was confirmed subjectively by a comparative consumer test in which 150 female subjects were asked to assess the product against their regular skin cream, under a series of headings describing subjective attributes. In each case, the panellists were asked to apply a score on a 5 point scale (0=disagree, product totally unacceptable; 5=agree, product excellent).

The results, which include an average of scores obtained under each heading, are summarised in the following Table:

| Subjective Attribute | Average Panel Scores (0 to 5) | | w/o HIPE cream significantly better than regular cream at P= |
|---|---|---|---|
| | Regular cream | w/o HIPE cream | |
| Does not leave the skin greasy | 3.82 | 4.58 | 0.01 |
| Impression of freshness when applied | 4.16 | 4.71 | 0.01 |
| Pleasant to use | 4.29 | 4.60 | 0.10 |
| Long lasting freshness impression | 3.97 | 4.43 | 0.05 |

It can be concluded from these results that the w/o HIPE cream was superior in all respects to the creams usually employed by the panellists, and was generally very well liked.

The efficacy of the w/o HIPE cream was also assessed objectively under the following headings:

1. Moisturising efficacy

The moisturising efficacy of the w/o HIPE cream was substantiated in vivo on human subjects using skin impedance measurements and transepidermal water-loss measurements.

(a) Impedance

Skin impedance was measured by the method of Clar et al, J.Soc. Cosmet. Chem., (1975), 26, 337-353, which equates electrical impedance of skin with its moisture content. A decrease in skin impedance is indicative of an increase in moisture content.

The moisturising efficacy of the w/o HIPE cream was accordingly compared with that of three commercially available brands of cream, each of which claimed to be a moisturising cream. It was demonstrated that the w/o HIPE cream induced a marked decrease in skin impedance indicative of a substantial moisturising effect, whereas none of the commercial moisturising creams showed a significant reduction in impedance, indicating that they have little or no true moisturising effect.

(b) Transepidermal water loss

Living skin perspires continuously and it is possible to monitor this water loss by means of a hygrometric sensor attached to the skin. A barrier cream is one which is able to impede water loss from the skin surface. The barrier effect of the w/o HIPE cream was accordingly compared with that of the three commercially available moisturising creams: it was shown following statistical analysis of the results that the w/o HIPE cream significantly reduced transepidermal water loss, whereas the commercial creams did not.

2. Skin cooling effect (freshness)

When a cream is applied topically to the skin, evaporation of water causes a drop in skin temperature due to the loss of skin calories by latent heat of evaporation. This cooling effect is recognised by the user as freshness.

The freshness sensation can be substantiated objectively by measurement of skin temperature using a telethermometer. The freshness following application of the w/o HIPE cream was compared with that following application of the three different commercially available skin moisturising creams.

From the telethermometer readings, it was established the w/o HIPE cream generated the greatest fall in skin temperature which substantiated the subjective observations of the panel who reported that the w/o HIPE cream produced the most striking sensation of freshness.

EXAMPLES 2 & 3

Examples 2 and 3 illustrate moisturising lotions.

| | % w/w | |
|---|---|---|
| | Ex. 2 | Ex. 3 |
| ARLACEL 987 | 3 | — |
| IMWITOR 780K | — | 3 |
| ISOPAR L | 15 | 15 |
| BENTONE 38 | 0.3 | 0.4 |
| Magnesium sulphate | 0.5 | — |
| Magnesium chloride | — | 0.5 |
| Triethanolamine lactate - 50%: pH 5.5 (moisturising agent) | 6 | 6 |
| Para P[(1)] | 0.1 | 0.1 |
| 1,3-butylene glycol | 3 | 3 |
| Water | 72.1 | 72.0 |

[(1)]propyl p-hydroxybenzoate.

The oil is mixed with the emulsifier, the Para P added and dissolved at a temperature of 50°-60° C. The BENTONE 38 is then added to provide the oily phase. The aqueous phase containing the magnesium salt, the lactate and the glycol are heated gently at 45°-50° C. Finally, the emulsion is prepared after cooling by emulsifying the aqueous phase with the oily phase to provide a water-in-oil emulsion at a temperature no higher than 50° C.

EXAMPLE 4

An emulsion having the following formulation as a further example of a skin moisturising lotion for topical application is prepared by the method described for Examples 2 and 3. It contains the following ingredients:

| Ingredients | | % w/w |
|---|---|---|
| O | IMWITOR 780K | 3 |
| | LYTOL - ex Witco | 15 |
| | Para P - ex Rhone Poulenc | 0.1 |
| | BENTONE 38 | 0.5 |
| A | Magnesium bromide | 1.0 |
| | Sodium pyrollidone carboxylate (Na PC) (moisturising agent) (50% in water) | 4 |
| | 1,3-butylene glycol | 3 |
| | Collagen hydrolysate | 3 |
| | Para M | 0.2 |
| | Water | 70 |

| Ingredients | % w/w |
|---|---|
| Perfume | 0.2 |

O — Oily phase
A — Aqueous phase

EXAMPLES 5 TO 7

These emulsions illustrate the formulation of moisturising creams for topical application to the skin:

| | | Example 5 | Example 6 | Example 7 |
|---|---|---|---|---|
| O | BRIJ 92 | 3 | — | — |
| | ARLACEL 80 | — | 3 | — |
| | SIMUSOL 92 | — | — | 3 |
| | ISOPAR L - ex Esso | 5 | — | — |
| | PARLEAM - ex Nichiyu | 5 | — | 5 |
| | LYTOL - ex Witco | — | 10 | — |
| | WM1 oil - ex BP | — | — | 5 |
| | PARA P - ex Rhone Poulenc | 0.1 | 0.1 | 0.1 |
| | BENTONE 38 | 0.6 | 0.8 | 1 |
| A | Magnesium nitrate hexahydrate | 0.4 | — | — |
| | Magnesium chloride hexahydrate | — | 0.5 | — |
| | Magnesium sulphate heptahydrate | — | — | 2 |
| | Na PC (50%) | 4 | 4 | 4 |
| | 1,3-butylene glycol | 3 | 3 | 3 |
| | Collagen hydrolysate | 3 | 3 | 3 |
| | Na glutamate | — | 2 | 2 |
| | PARA M - ex Rhone Poulenc | 0.2 | 0.2 | 0.2 |
| | Water | 75.5 | 73.2 | 71.5 |
| | Perfume | 0.2 | 0.2 | 0.2 |

EXAMPLE 8

This example also illustrates the formulation of a moisturising cream for topical application to the skin:

| | Ingredients | % w/w |
|---|---|---|
| O | MONTANE 70 | 3 |
| | LYTOL | 5 |
| | MARCHOL 82 | 5 |
| | CEREWAX L | 0.2 |
| | MODULAN | 1 |
| | PARA P | 0.1 |
| | BENTONE 38 | 2 |
| A | Magnesium acetate | 0.8 |
| | Na PC (50%) | 4 |
| | 1,3-butylene glycol | 3 |
| | Collagen hydrolysate | 3 |
| | Na glutamate | 1 |
| | PARA M | 0.2 |
| | Water | 71.5 |
| | Perfume | 0.2 |

EXAMPLE 9

This example also illustrates the formulation of a moisturising cream for topical application to the skin:

| | Ingredients | % w/w |
|---|---|---|
| O | CRILL 6 | 3.5 |
| | ISOPAR L | 5 |
| | PARLEAM | 5 |
| | CEREWAX L | 0.2 |
| | MODULAN | 1 |
| | PARA P | 0.1 |
| | BENTONE 38 | 1.5 |
| A | Magnesium bromide hexahydrate | 0.2 |
| | Na PC (50%) | 4 |
| | Glycine | 5 |
| | PARA M | 0.2 |
| | Water | 74.1 |

| Ingredients | % w/w |
|---|---|
| Perfume | 0.2 |

What is claimed is:

1. A high internal phase water-in-oil emulsion stable through at least two freeze thaw cycles consisting essentially of:

(a) from 1.4 to 24.3% by weight of a branched chain non-polar oil;

(b) from 0.5 to 10% by weight of a non-anionic liquid emulsifier having an HLB value of from 1 to 7;

(c) from 0.1 to 5% by weight of a reaction product of a sodium magnesium-fluorolithosilicate trioctahedral montmorillonite clay and the quaternary ammonium salt having the formula:

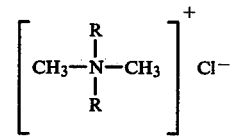

where R represents hydrogenated tallow fatty acid radicals;

(d) from 0.1 to 5% by weight of a water-soluble magnesium salt; and (e) from 0.1 to 97.9% by weight of water;

the aqueous phase forming from 75 to 98% by volume, and the oily phase forming from 25 to 2% by volume of the emulsion.

2. The emulsion according to claim 1, wherein the oil forms from 2 to 24% by weight of the emulsion.

3. The emulsion according to claim 1, wherein the oil forms from 2 to 15% by weight of the emulsion.

4. The emulsion according to claim 1, wherein the emulsifier forms from 2 to 5% by weight of the emulsion.

5. The emulsion according to claim 1, wherein the reaction product of the sodium magnesium-fluorolithosilicate trioctahedral montmorillonite clay and the quaternary ammonium salt forms from 0.1 to 1.0% by weight of the emulsion.

6. The emulsion according to claim 1, wherein the magnesium salt is selected from the group consisting of magnesium sulphate, magnesium sulphate monohydrate, magnesium sulphate heptahydrate and mixtures thereof.

7. The emulsion according to claim 1, which contains from 0.1 to 5% by weight of magnesium sulphate heptahydrate.

8. The emulsion according to claim 7, which contains from 0.1 to 2% by weight of magnesium sulphate heptahydrate.

9. The emulsion according to claim 1, wherein water forms from 1 to 97% by weight of the emulsion.

10. The emulsion according to claim 9, wherein water forms from 60 to 95% by weight of the emulsion.

11. The emulsion according to claim 1, wherein the aqueous phase forms from 80 to 97% by volume of the emulsion.

12. The emulsion according to claim 1, wherein the oily phase forms from 20 to 3% by volume of the emulsion.

13. The emulsion according to claim 1, which contains by weight of the emulsion:
(a) from 2 to 15% of a branched chain non-polar oil;
(b) from 2 to 5% of a non-anionic liquid emulsifier having an HLB value of from 1 to 7;
(c) from 0.1 to 5% of a reaction product of a sodium magnesium-fluorolithosilicate trioctahedral montmorillonite clay and the quaternary ammonium salt having the formula:

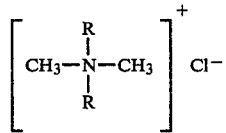

where R represents hydrogenated tallow fatty acid radicals;
(d) from 0.1 to 5% of magnesium sulphate heptahydrate; and
(e) from 60 to 95% of water.

14. The emulsion according to claim 1, which is a cream, gel or lotion.

15. A process for preparing a water-in-oil emulsion according to claim 1, which comprises the steps of:
(a) mixing the reaction product of a sodium magnesium-fluorolithosilicate trioctahedral montmorillonite clay and the quaternary ammonium salt having the formula:

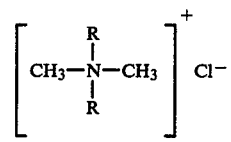

where R represents hydrogenated tallow fatty acid radicals, with a non-anionic liquid emulsifier having an HLB value of from 1 to 7 and a branched chain non-polar oil to provide an oily phase; and
(b) homogenising the oily phase with an aqueous phase comprising an aqueous solution of a water-soluble magnesium salt to provide a water-in-oil emulsion in which the aqueous phase forms from 75 to 98% by volume of the emulsion and the oily phase forms from 2 to 25% by volume of the emulsion.

16. A closed container containing an emulsion according to claim 1.

* * * * *